US008163005B2

(12) United States Patent  (10) Patent No.: US 8,163,005 B2
Lawrence-Brown  (45) Date of Patent: Apr. 24, 2012

(54) VASCULAR BAND

(75) Inventor: Michael Lawrence-Brown, City Beach (AU)

(73) Assignees: William A. Cook Australia Pty. Ltd., Queensland (AU); Cook Medical Technologies LLC, Bloomington, IN (US)

( * ) Notice: Subject to any disclaimer, the term of this patent is extended or adjusted under 35 U.S.C. 154(b) by 634 days.

(21) Appl. No.: 12/074,279

(22) Filed: Mar. 3, 2008

(65) Prior Publication Data

US 2008/0215134 A1  Sep. 4, 2008

Related U.S. Application Data

(60) Provisional application No. 60/904,458, filed on Mar. 2, 2007.

(51) Int. Cl.
*A61F 2/06* (2006.01)
(52) U.S. Cl. .................. 623/1.34; 606/151
(58) Field of Classification Search .......... 606/151; 623/1.26, 1.34
See application file for complete search history.

(56) References Cited

U.S. PATENT DOCUMENTS

| 3,435,823 A | 4/1969 | Edwards |
| 4,696,288 A | 9/1987 | Kuzmak et al. |
| 4,904,254 A | 2/1990 | Lane |
| 5,752,966 A * | 5/1998 | Chang ............... 606/151 |
| 5,843,170 A * | 12/1998 | Ahn ................ 623/1.34 |
| 2007/0244546 A1 * | 10/2007 | Francis ............. 623/1.26 |

FOREIGN PATENT DOCUMENTS

| WO | WO 9739687 | 10/1997 |
| WO | WO 99/34748 | 7/1999 |
| WO | PCT/US2008/002800 | 8/2008 |

OTHER PUBLICATIONS

David W. Chang, Enabling sutureless vascular bypass grafting with the exovascular sleeve anastomosis, Journal of Vascular Surgery, vol. 32, No. 3, Sep. 2000, p. 524-530.
Scarcello, et al, Experimental Study of a New Vascular Anastomotic.., Annals of Vascular Surgery, vol. 21, No. 3, Apr. 6, 2007,p. 346-351, Quality Med Publ., St. Louis,MO, US.
Lawrence-Brown, et al, Hybrid Open-Endoluminal Technique for Repair of Thoracoabdominla Aneurysm..., Journal of Endovascular Therapy, Dec. 2000, vol. 7 Issue 6, p. 513-519.

* cited by examiner

*Primary Examiner* — Thomas J Sweet
*Assistant Examiner* — Matthew Schall
(74) *Attorney, Agent, or Firm* — Richard J. Godlewski

(57) ABSTRACT

A vascular band (1) comprises a biocompatible flexible material (2) and a plurality of radiopaque bars (4) extending transversely across the width of the material and spaced apart along the length of the biocompatible material. The bars provide some rigidity to the flexible material in the width direction thereby preventing buckling of the band in use and the radiopaque nature of the bars enable visualization of a landing zone for a stent graft during deployment thereof. The bars can be crimped or woven into the material. The band can be stitched, stapled, or hooked around a vessel.

11 Claims, 5 Drawing Sheets

VASCULAR BAND

CROSS-REFERENCE TO RELATED APPLICATIONS

This application claims priority of provisional application Ser. No. 60/904,458, filed Mar. 2, 2007.

TECHNICAL FIELD

This invention relates to a medical device and more particularly to a device for use with vascular or endovascular surgery.

BACKGROUND OF THE INVENTION

Endovascular surgery involves the placement of stents or stent grafts into the vasculature of a patient and in one form is particularly directed to the deployment of stent grafts into vessels of the body to span or bridge a defect in the vasculature. Such a defect can for instance be an aneurysm where part of the wall of the vessel has weakened and the vessel has expanded in that region. Placement of endovascular stent grafts in such regions requires a stable landing zone for proximal and distal ends of a stent graft so that the stent graft engages securely against the wall of the vessel preventing migration of the stent graft and endoleaks around the stent graft. Such endoleaks can exacerbate an aneurysm problem.

In some regions of the vasculature, especially in the proximity of essential vessels such as near the renal arteries, often there is only a relatively short landing zone for the proximal end of a stent graft and this can require that a stent graft should extend beyond the renal arteries which requires branch grafting or fenestrations to allow access to the renal arteries. Such a problem could be avoided if a stable landing zone was provided in a juxta-renal position such as just below the renal arteries.

It is the object of this invention to provide a device which can improve the chance of providing a successful landing zone for a stent graft or at least provide a physician with a useful alternative.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

SUMMARY OF THE INVENTION

In one form therefore the invention is said to reside in a vascular band comprising a substantially rectangular portion of a flexible biocompatible material, the biocompatible material being substantially inextensible, the band having a width and a length, the length being substantially greater than the width and at least three radiopaque bars extending transversely across the width of the material and spaced apart along the length of the biocompatible material, the bars providing some rigidity to the flexible material in the width direction.

The term substantially inextensible in relation to the flexible biocompatible material is intended to mean that having regard to the normal forces on the material in its intended use that the material will not stretch. In the use of the material as an aortic band according to the present invention the vascular band, under the action of blood pressure and the force applied by self expanding stents and balloon expandable stents, the length and hence diameter of the installed band should not change. This assists with the prevention of expansion of a vessel wall around which it is placed thereby providing a stable landing zone and assisting in preventing endoleaks and migration of a stent graft placed into the vessel.

Preferably the bio-compatible flexible material is selected from the group comprising Dacron, Thoralon™, a polyurethane based material, and polytetrafluoroethylene.

The band can have a width of from 10 mm to 40 mm and a length of from 40 to 200 mm. Where the band is intended for use on a juxtarenal portion of the aorta it can comprise a width of from 20 mm to 40 mm and a length of from 75 to 200 mm. Where the band is intended for use on a portion of the iliac artery of a patient it can comprise a width of from 15 mm to 25 mm and a length of from 40 to 100 mm.

The bars can be formed from a material selected from stainless steel, Nitinol™, gold or tantalum.

The bars can be spaced apart along the length of the material by a distance of from 10 to 40 mm.

In one embodiment the bars can be crimped onto the material. Alternatively the bars can be sewn, woven or stitched into or through the material across the width thereof.

In a preferred embodiment the band has a length substantially equal to the outside circumference of the vessel to which the band is to be applied and the bars extending transversely across the width are placed at each end and at least substantially midway along the length.

In another preferred embodiment the band has a length greater than the outside circumference of the vessel to which the band is to be applied and the band comprises a variable length fastening means to enable to band to be fastened around the vessel without the necessity of knowing the outer circumference thereof.

The variable length fastening means can be selected from sutures, surgical staples and hook and loop fastening systems. The hook and loop fastening system can comprise a row of hooks on one end of the band and an array of loops on the other end of the band.

In a preferred embodiment the band has a length greater than the outside circumference of the vessel to which the band is to be applied, one of the bars being fastened to the band at a first end thereof and the other end of the band defining a tail portion which is free of bars and further comprising markings thereon relating to the diameter of a vessel upon which the band is placed, the markings being measured from the first end and whereby the measurement relating to the diameter is observed where the first end engages the tail portion.

In an alternative form the invention comprises a vascular band comprising a biocompatible flexible material, the band having a width direction and a length direction, the length of the band in the length direction being at least four times greater in length than the width of the band in the width direction and a plurality of radiopaque bars extending transversely across the width of the material, the radiopaque bars being fastened to the band and spaced apart along the length of the biocompatible material, the bars providing some rigidity to the flexible material in the width direction thereby preventing buckling of the band in use and the radiopaque bars enabling visualisation of a landing zone for a stent graft during deployment thereof and wherein the band has a length greater than the outside circumference of the vessel to which the band is to be applied, one of the bars being fastened to the band at a first end thereof and the other end of the band defining a tail portion which is free of bars and further comprising markings thereon relating to the diameter of a vessel upon which the band is placed, the markings being measured from the first end and whereby the measurement relating to the diameter is observed where the first end engages the tail portion.

Where a broader landing zone is desired or required there can be placed two or more bands which may for instance slightly overlap each other.

It will be seen that by this invention there is provided a device which can be placed around the vessel to such that the vessel is supported in such a manner as to provide a landing zone within the vessel for the deployment of a stent graft.

The band can be applied by open surgical techniques or by the use of laparoscopic techniques.

The vascular band according to the present invention has several distinct additional advantages. By the use of the transverse bars the flexible material will not buckle or fold in the transverse direction as it is placed around the vessel thereby providing a smoother and more stable and reliable landing zone. The use of the radiopaque bands also means that during the deployment of the stent graft the position of the vascular band can be observed using radiographic techniques and the proximal end, for instance, of the stent graft accurately placed for best prevention of migration and endoleaks.

As discussed above the vascular band of the present invention is particularly adapted for placement just below the renal arteries as an aortic band but can also be used in the iliac arteries as an iliac band or in other parts of the human or animal body. Other sites can include the ascending aorta, aortic arch and the upper abdominal or distal thoracic aorta.

BRIEF DESCRIPTION OF THE DRAWING

This then generally describes the invention but to assists with understanding reference will now be made to the accompanying drawings which show preferred embodiments of the invention.

In the drawings.

DETAILED DESCRIPTION

Figure 1:
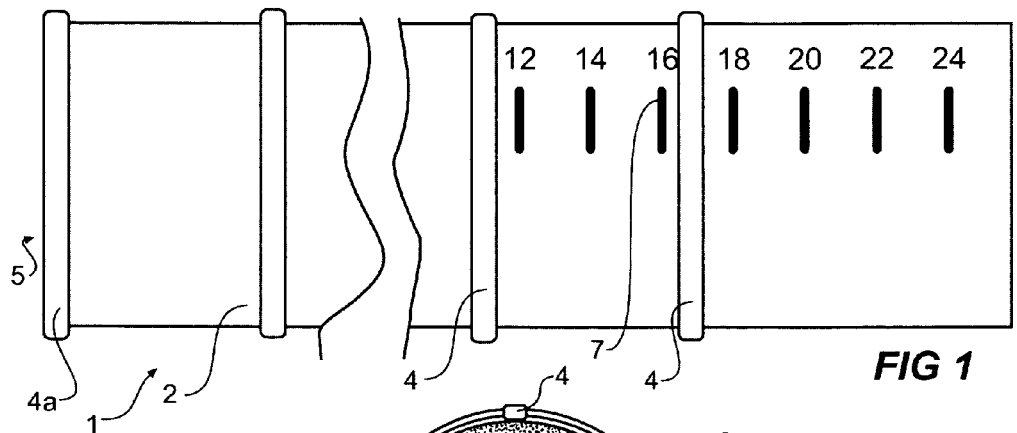
FIG. 1 shows a first embodiment of aortic band according to the present invention.
Figure 2:
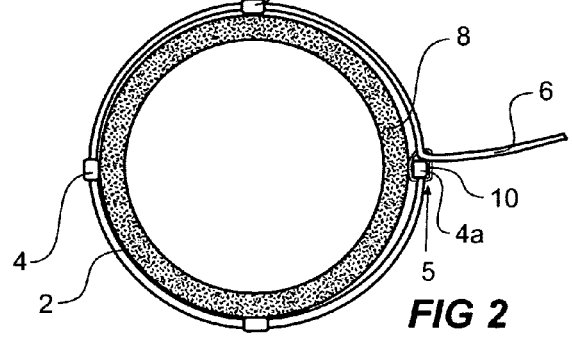
FIG. 2 shows the use of the aortic band of FIG. 1 placed around a vessel.

Now looking more closely at the drawings and in particular the first embodiment of vascular band shown in FIGS. 1 and 2.

The vascular band 1 of this embodiment comprises a length of flexible bio-compatible material 2 which is approximately four times longer than it is wide. A number of transverse bars 4 of a radiopaque material such as stainless steel extend across the full width of the material 2 and are crimped onto the flexible material and a tail 6 is left at one end. The vascular band has markings 7 upon it which enable the physician when placing the band around the vasculature to know the diameter of the band and hence the vessel upon which it is placed to assist with selection and placement of the subsequent stent graft. The markings correspond to the diameter of the vessel after placement. In this example the band is for a iliac artery which is expected to have a diameter in the range of from 12 to 24 millimeters. This band may have a width of width of 15 mm and a length of 100 mm allowing for a tail 19 which can be cut off or left in place after placement. The bars are spaced apart by about 20 mm.

As can be seen in FIG. 2 the vascular band 1 is wrapped around a vessel 8 and a surgical staple or stitching 10 is used to connect the end 5 to the tail end 6 so that the vascular band is a snug fit around the vessel. A portion of the tail extends out and can be left. A stent graft can then be deployed into the vessel 8 as discussed in relation to FIGS. 11 and 12 below. The tail 6 allows a range of diameters of vessel to be accommodated.

Figure 3:
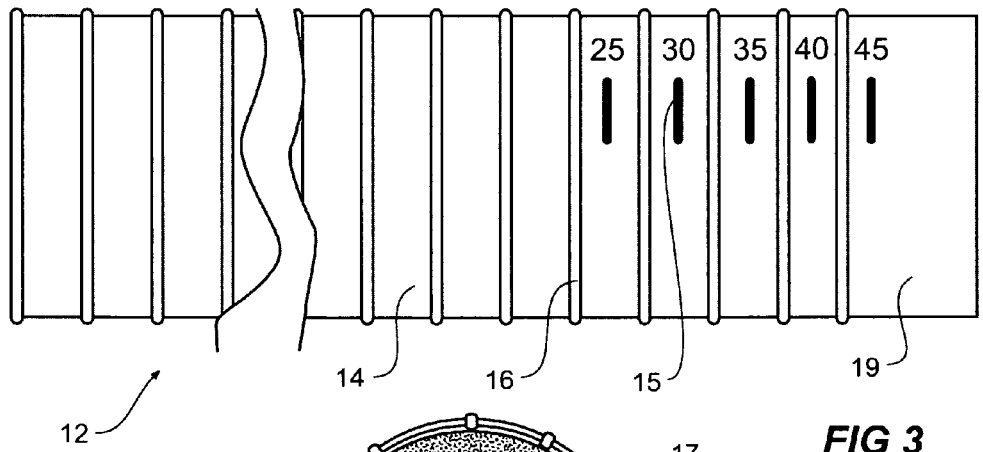
FIG. 3 shows an alternative embodiment of vascular band according to the present invention.
Figure 4:
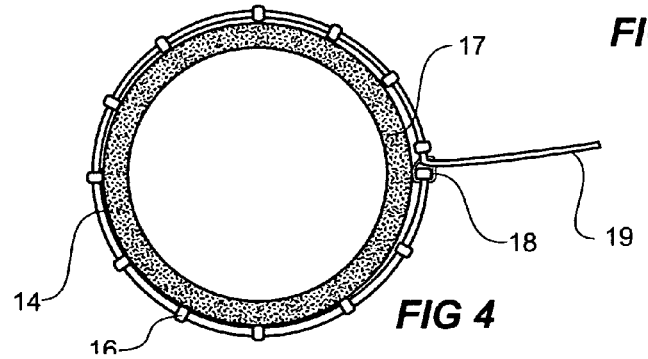
FIG. 4 shows the use of the vascular band of FIG. 3 around a vessel of the human or animal body.

FIGS. 3 and 4 show an alternative embodiment. In this embodiment the vascular band 12 includes a flexible material 14 which is substantially longer than it is wide and includes bars 16 extending transversely across the full width of the material at regular intervals along the length. There is a tail 19 left free bars at one end of the band. The vascular band has markings 15 upon it which enable the physician when placing the band around the vasculature to know the diameter of the band and hence the vessel upon which it is placed to assist with selection and placement of the subsequent stent graft. The markings correspond to the diameter of the vessel after placement and can be observed during placement. In this example the band is for aorta in the region of the renal arteries which is expected to have a diameter in the range of from 25 to 45 millimeters. This band may have a width of 40 mm and a length of 200 mm. The bars are spaced apart by about 15 mm.

As can be seen in FIG. 4 again the vascular band 12 is wrapped around the vessel 17 and a surgical staple or stitching 18 is used to fasten it around the vessel to give a snug fit to the vessel.

Figure 5:
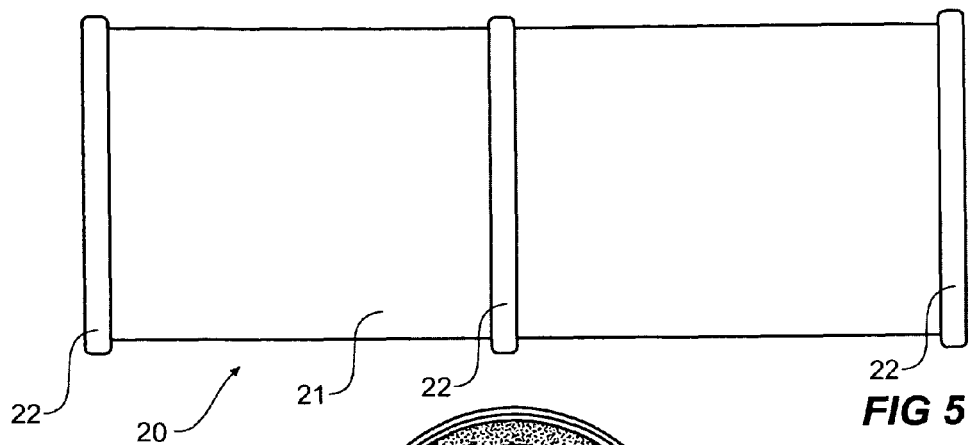
FIG. 5 shows a still further embodiment of vascular band according to the present invention.
Figure 6:
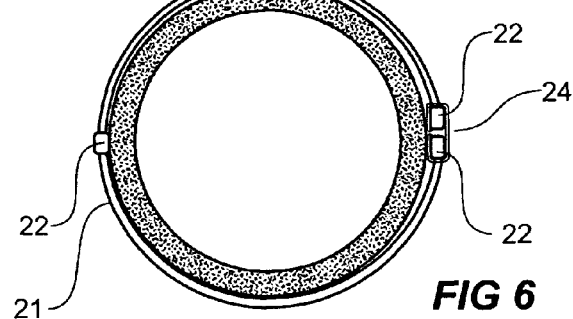
FIG. 6 shows the use of the vascular band of FIG. 5 around a vessel of the human or animal body.

FIGS. 5 and 6 show a still further embodiment of vascular band according to the inventions. In this embodiment the vascular band 20 incorporates three bars 22 with one at each end and one in the middle. The bars extend across the full width of the material In this embodiment the vascular band is made substantially at the correct length for the circumference of the vessel so that when placed around the vessel the terminal bars 22 then can be connected by means of a surgical staple or stitching 24 and the central transverse bar 22 is substantially diametrically opposed to the connection 24.

Figure 7:
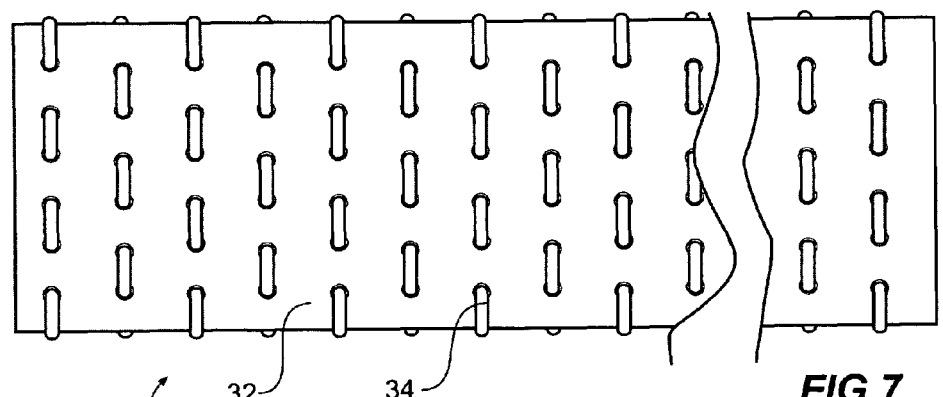
FIG. 7 shows a still further embodiment of vascular band according to the present invention.

FIG. 7 shows a still further embodiment of vascular band according to the present invention. In this embodiment the vascular band 30 includes a flexible graft of a biocompatible graft material 32 with a plurality of transverse bars 34 or rods. The transverse bars or rods 34 are interwoven or stitched into and across the full width of the graft material 32. By this arrangement a flexible band is provided which can be wrapped around a vessel of the human or animal body and which will not buckle in the transverse direction thereby providing a surgical support for a landing zone for an endovascular graft.

Figure 8:
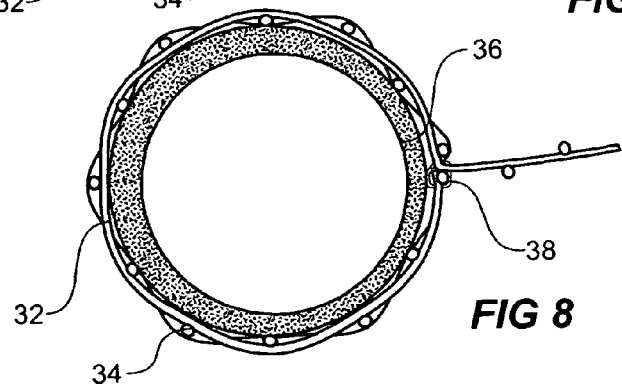
FIG. 8 shows the use of the vascular band of FIG. 7 around a vessel of the human or animal body.

FIG. 8 shows the embodiment of vascular band shown in FIG. 7 around a vessel 36. A surgical staple 38 is used to fasten the band around the vessel at the necessary length. The bars or rods 34 extend along the length of the vessel and prevent the band buckling and provide a radiopaque marking for defining the landing zone for an endovascularly deployed stent graft.

Figure 9A:
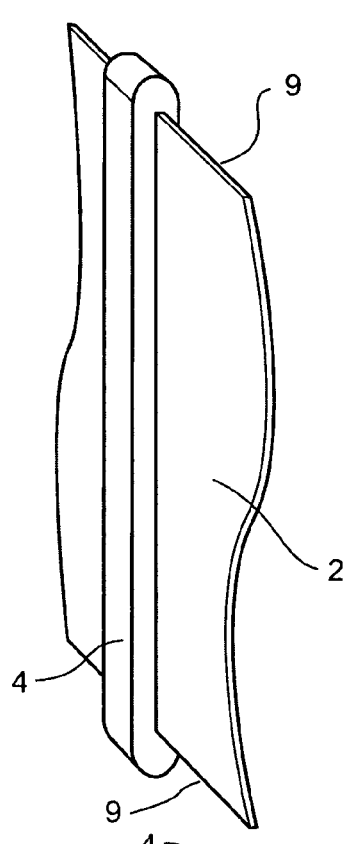
FIGS. 9A and 9B show detail of the placement of a transverse bar onto a portion of flexible material.
Figure 9B:
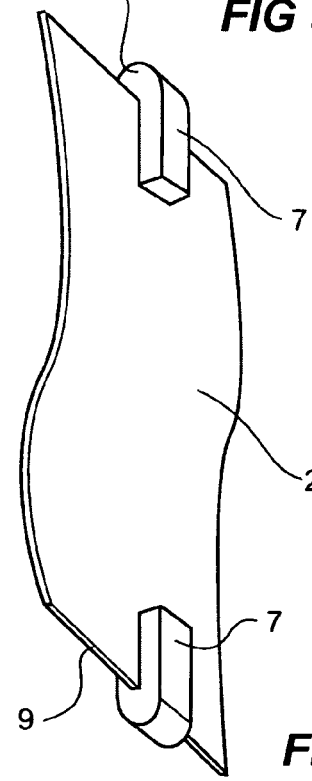

FIGS. 9A and 9B show a portion of the vascular band shown in FIG. 1 showing detail of the means by which the bars are crimped onto the flexible bio-compatible material. The bio-compatible material 2 has a bar 4 crimped onto it. The bar includes folded over ends 7 which are crimped over the sides 9 of the flexible material 2 to the back of the flexible material to enable the bar 4 to grip onto the flexible material.

Figure 10A:
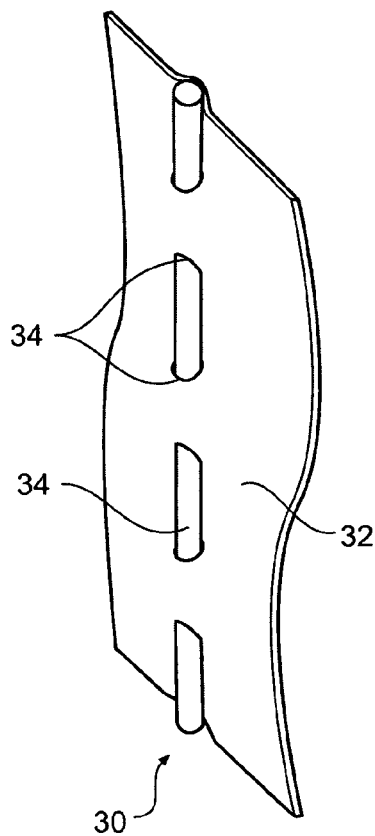
FIGS. 10A and 10B show alternative methods of placing a transverse bar onto the flexible biocompatible material.

FIG. 10A shows a detailed view of the vascular band of the embodiment shown in FIGS. 7 and 8. In this embodiment the bar 34 is threaded into apertures 35 in the material 32 so that it extends transversely across the material 32.

Figure 10B:
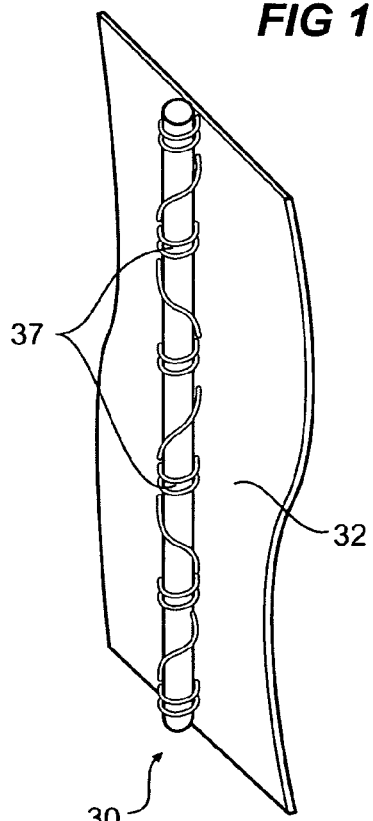

FIG. 10B shows a detailed view of an alternative embodiment of vascular band showing an alternative method of fastening a bar to the biocompatible material. In this embodiment the bar 34 is fastened to the material 32 by the means of stitching 37.

Figure 11:
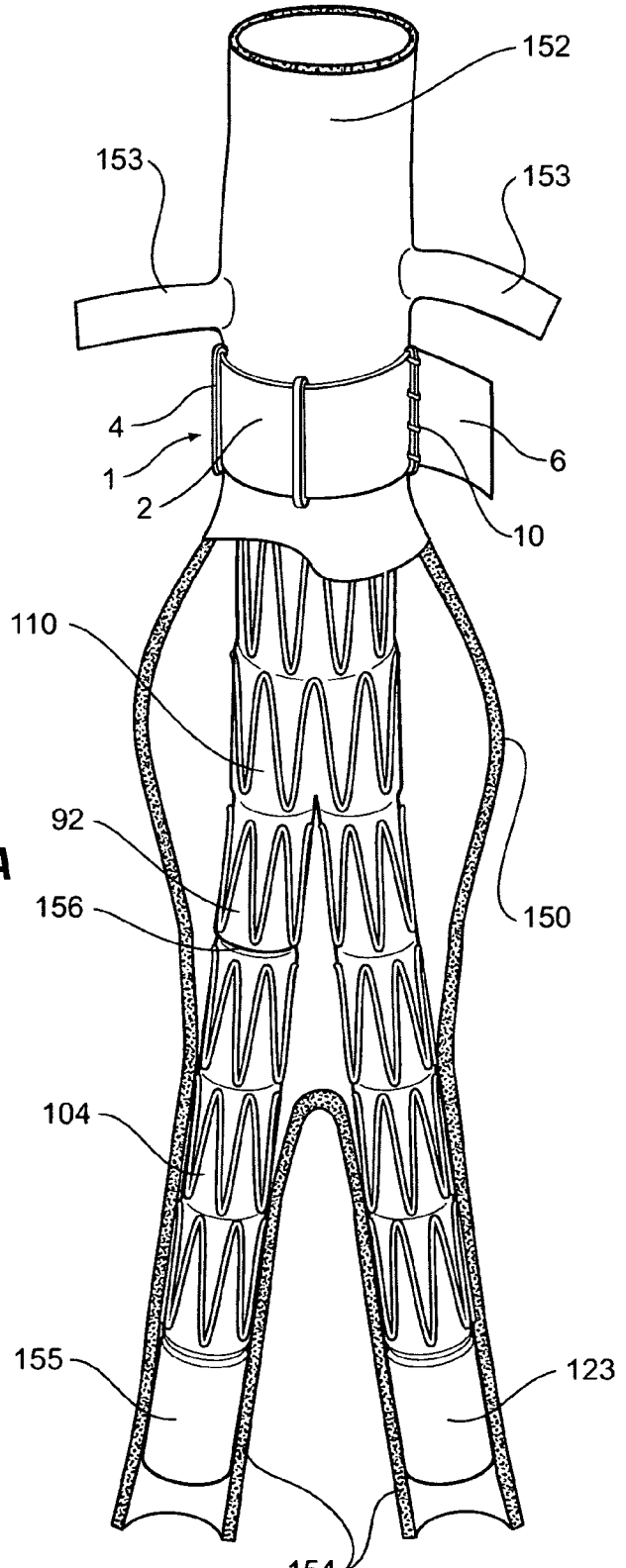
FIG. 11 shows a schematic view of the placement of a vascular band of the type shown in FIG. 1 onto the vasculature of a patient adjacent the renal arteries.

FIG. 11 shows a deployed stent graft within an aorta with an aneurysm and incorporating a vascular band according to the present invention.

The aneurysm 150 is a ballooning of the aorta 152 between the renal arteries 153 and the iliac arteries 154. The stent graft 110 (as shown in more detail in FIG. 12) is deployed into the aorta so that it spans the aneurysm and allows blood flow from the aorta to the two iliac arteries 154.

An aortic band 1 of the type shown in FIG. 1 has been placed just distal of the renal arteries 153 and around the aorta 152 with the bars 4 substantially in line with the longitudinal direction of the aorta. Surgical staples 10 have been used to fasten the vascular band 1 in place and the tail 6 of the band extends out from the connection.

The proximal portion 114 (see FIG. 12) of the stent graft 110 which has the stent on the inside bears against the wall of the aorta 152 in the region of placement of the vascular band 1 above the aneurysm and below the renal arteries so that a good seal is obtained. The exposed zigzag stent 115 (see FIG. 12) which extends beyond the portion 114 extends over the entrances to the renal arteries but, as the wire of the stent is thin, occlusion does not occur. The distal end 123 of the long leg 120 of the stent graft 110 seals against the wall of one of the iliac arteries and the distal end 155 of the extension leg stent graft 121 bears against the wall of the other iliac artery.

Figure 12:
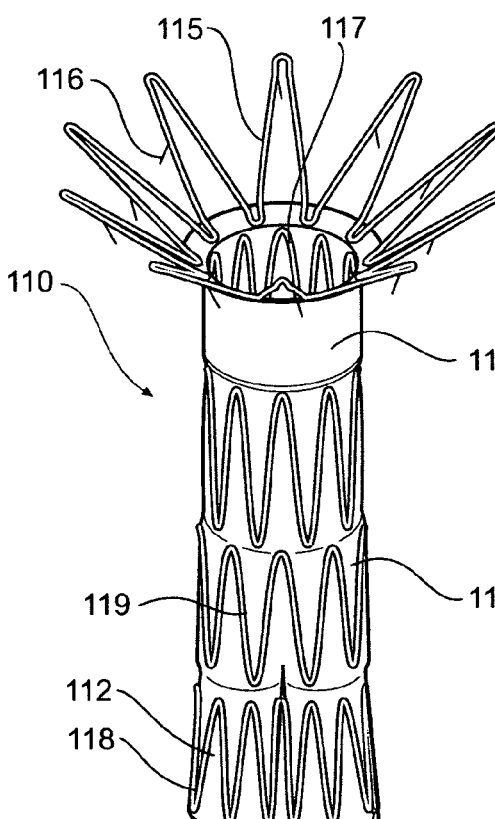
FIG. 12 shows a stent graft of the type for which the use of an aortic landing zone band is useful.

FIG. 12 shows an embodiment of a bifurcated stent graft with an extension stent graft suitable for placement into an aorta and engaging against the aorta where an aortic band according to the present invention has been placed. The bifurcated stent graft 110 has a generally inverted Y-shaped configuration having a body portion 111, a shorter leg 112 and a longer leg 120. The body of the stent graft is constructed from a tubular woven synthetic material such as Dacron™. At the proximal end 114 of the stent graft 110 is a first zigzag stent 115 which extends beyond the end of the stent graft and has distally extending barbs 116. The stent graft has a number of zigzag stents mounted to it and extending along its length. The stent 117 nearest the proximal end 114 is inside the tubular material so that the outside presents a smooth surface which in use engages against the inner wall of the vessel into which it is deployed to provide a barrier to endoleaks. The terminal stent 118 nearest the distal end of the shorter leg is outside the tubular material so that the inside presents a smooth surface which in use engages against the outside of the proximal end of a leg extension stent graft 121. Between these terminal stents the rest of the stents 119 are arranged on the outside of the tubular material so that they present minimal restriction to the flow of blood through the stent graft and present minimal sites for the growth of thromboses within the stent graft.

Extension leg stent graft 121 is adapted for fitting into the shorter leg. The extension stent graft 121 is constructed from a tubular synthetic material such as Dacron and has terminal internal stents 122 and a plurality of external intermediate stents 124.

In use the stent graft according to this embodiment of the invention is adapted for fitting into aorta such that the end 114 is just distal of the renal arteries and the first exposed zigzag stent 115 extends up to or over the renal arteries. As it is constructed from thin wire it does not obstruct the renal arteries if it extends over them. The longer leg 120 extends down one of the iliac arteries and the shorter leg terminates in the aorta just short of the other iliac artery. The extension stent graft when deployed extends down the other iliac artery.

A vascular band for use in the juxtarenal position of the aorta may have a length of from 75 to 200 mm and a width of from 20 to 30 mm. A range of bands may be manufactured with 15 mm length changes such as bands with lengths of 75 mm, 90 mm, 105 mm, 120 mm, 135 mm and 150 mm to accommodate the expected range of vessel diameters. A vascular band for the iliac arteries may have a length of from 40 to 60 mm and a width of from 15 to 25 mm. A range of bands may be manufactured with 5 mm length changes such as bands with lengths of 40 mm, 45 mm, 55 mm and 60 mm to accommodate the expected range of vessel diameters.

Figure 13:
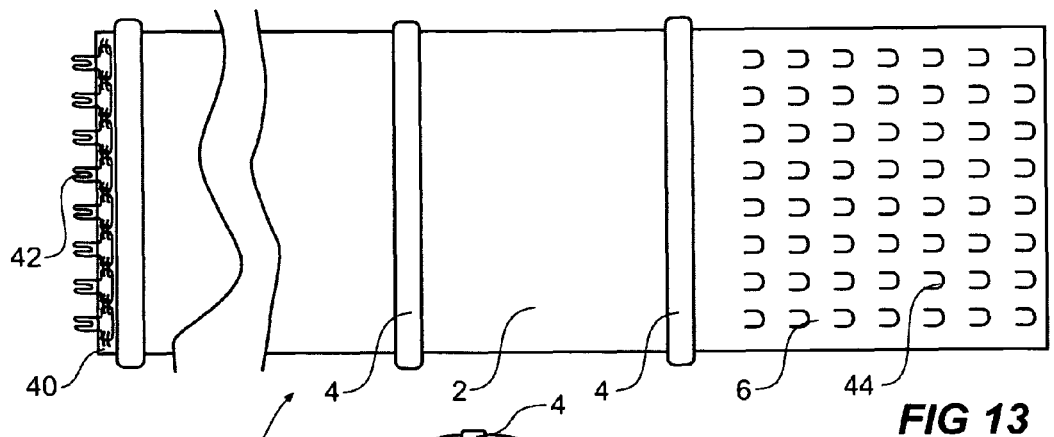
FIG. 13 shows a still further embodiment of vascular band with a first form of fastening system according to the present invention.
Figure 14:
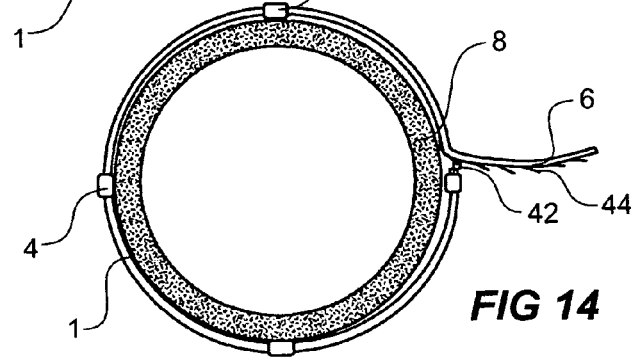
FIG. 14 shows the use of the vascular band of FIG. 13 around a vessel of the human or animal body.

FIG. 13 shows a still further embodiment of vascular band with a first form of fastening system according to the present invention and FIG. 14 shows the use of the vascular band of FIG. 13 around a vessel of the human or animal body. This embodiment is similar in many respects to that shown in FIG. 1 and the same reference numerals are used for corresponding items.

The vascular band 1 of this embodiment comprises a length of flexible bio-compatible material 2 which is approximately four to five times longer than it is wide. A number of transverse bars 4 of a radiopaque material such as stainless steel extend across the full width of the material and are crimped onto the flexible material at each and a tail 6 is left at one end and a short end 40 at the other end. On the short end 40 a row of hooks 42 are fastened and on the tail 6 an array of loops 44 is fastened. As can be seen in FIG. 14 the band 1 is wrapped around a vessel 8 and hooks 42 are engaged with whichever line of loops 44 of the array of loops are closest to the required circumference.

Figure 15:
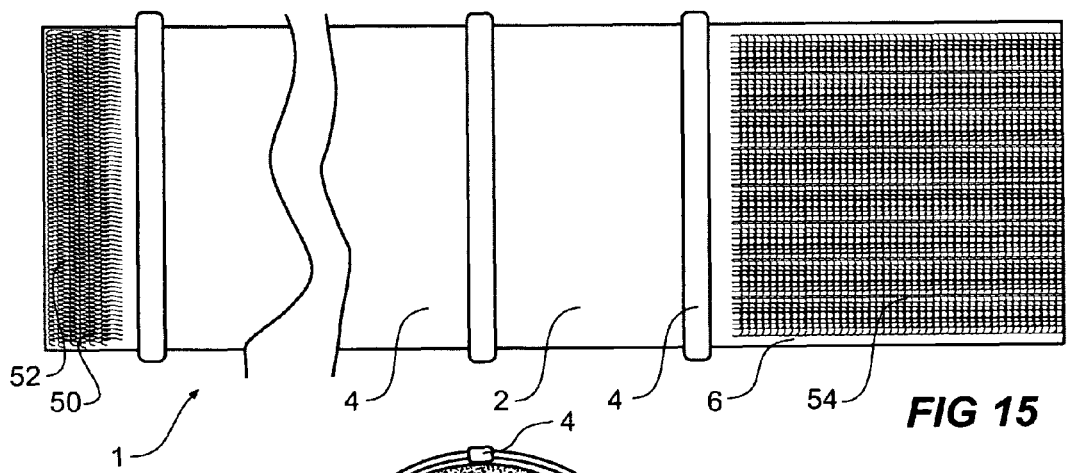
FIG. 15 shows a still further embodiment of vascular band with a second form of fastening system according to the present invention.
Figure 16:
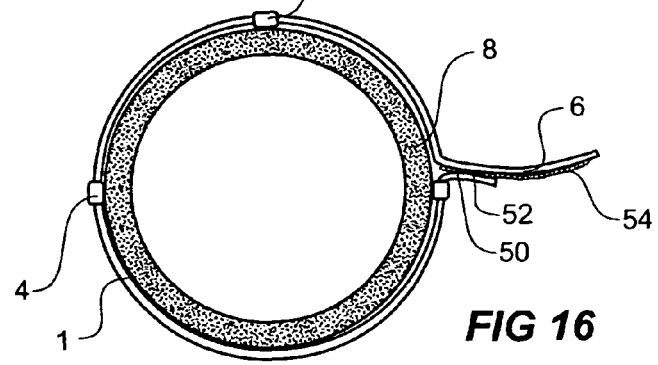
FIG. 16 shows the use of the vascular band of FIG. 15 around a vessel of the human or animal body.

FIG. 15 shows a still further embodiment of vascular band with a second form of fastening system according to the present invention and FIG. 16 shows the use of the vascular band of FIG. 15 around a vessel of the human or animal body.

This embodiment is similar in many respects to that shown in FIG. 1 and the same reference numerals are used for corresponding items.

The vascular band 1 of this embodiment comprises a length of flexible bio-compatible material 2 which is approximately four to five times longer than it is wide. A number of transverse bars 4 of a radiopaque material such as stainless steel extend across the full width of the material and are crimped onto the flexible material and a tail 6 is left at one end and a short end 50 at the other. On the short end 50 a portion of the hook part of a hook and loop fastener system is fastened and at the tail end 6 a portion of the loop part of a hook and loop fastener system is fastened.

As can be seen in FIG. 16 the band 1 is wrapped around a vessel 8 and the hooks portion of the hook and loop fastener system is engaged against the loops portion of the hook and loop fastener system to fasten the band around the vessel. Alternatively the hooks portion and the loops portions may be provided on opposite sides of the band.

Throughout this specification unless the context requires otherwise, the words 'comprise' and 'include' and variations such as 'comprising' and 'including' will be understood to imply the inclusion of a stated integer or group of integers but not the exclusion of any other integer or group of integers.

Throughout this specification various indications have been given as to the scope of this invention but the invention is not limited to any one of these but may reside in two or more of these combined together. The examples are given for illustration only and not for limitation.

What is claimed is:

1. A vascular band comprising a substantially rectangular portion of a flexible biocompatible material, the biocompatible material being substantially inextensible, the band having a width and a length, wherein the width is from 15 mm to 30 mm and the length is from 40 to 200 mm, and at least three radiopaque bars extending transversely across the full width of the material and spaced apart along the length of the biocompatible material, the radiopaque bars being fastened to the band, the bars providing some rigidity to the flexible material in the width direction and wherein the bars comprise folded over ends and are fastened to the band by being crimped onto the biocompatible material with the folded over ends over sides of the flexible biocompatible material and wherein the flexible biocompatible material is selected from the group comprising Dacron, a polyurethane based material and polytetrafluoroethylene.

2. A vascular band as in claim 1 wherein when the band is intended for use on a juxtarenal portion of the aorta it comprises a width of from 20 mm to 30 mm and a length of from 75 to 200 mm and when the band is intended for use on a portion of the iliac artery of a patient it comprises a width of from 15 mm to 24 mm and a length of from 40 to 100 mm.

3. A vascular band as in claim 1 wherein the bars are formed from a material selected from the group comprising stainless steel, nitinol, gold or tantalum.

4. A vascular band as in claim 1, wherein the bars are spaced apart along the length of the material by a distance of from 10 to 40 mm.

5. A vascular band as in claim 1 wherein the band has a length substantially equal to the outside circumference of the vessel to which the band is to be applied and the bars extending transversely across the width are placed at each end and at least substantially midway along the length.

6. A vascular band as in claim 1 wherein the band has a length greater than the outside circumference of the vessel to which the band is to be applied, one of the bars being fastened to the band at one end thereof and the other end of the band defining a tail portion which is free of bars.

7. A vascular band as in claim 1 wherein the band has a length greater than the outside circumference of the vessel to which the band is to be applied and the band comprises a variable length fastening arrangements to enable the band to be fastened around the vessel.

8. A vascular band as in claim 7 wherein the variable length fastening arrangement is selected from the group comprising a suture, surgical staples and hook and loop fastening systems.

9. A vascular band as in claim 8 wherein the hook and loop fastening system comprises a row of hooks on one end of the band and an array of loops on the other end of the band.

10. A vascular band as in claim 1 wherein the band has a length greater than the outside circumference of the vessel to which the band is to be applied, one of the bars being fastened to the band at a first end thereof and the other end of the band defining a tail portion which is free of bars and further comprising markings thereon relating to the diameter of a vessel upon which the band is placed, the markings being measured from the first end and whereby the measurement relating to the diameter is observed where the first end engages the tail portion.

11. A vascular band comprising a biocompatible flexible material, the flexible biocompatible material being selected from the group comprising Dacron, a polyurethane based material and polytetrafluoroethylene the band having a width direction and a length direction the length of the band in the length direction being about four times greater in length than the width of the band in the width direction and a plurality of radiopaque bars extending transversely across the full width of the material, the radiopaque bars being fastened to the band by being crimped thereto and spaced apart along the length of the biocompatible material, the bars providing some rigidity to the flexible material in the width direction thereby preventing buckling of the band in use and the radiopaque bars enabling visualization of a landing zone for a stent graft during deployment thereof and wherein the band has a length greater than the outside circumference of the vessel to which the band is to be applied, one of the bars being fastened to the band at a first end thereof and the other end of the band defining a tail portion which is free of bars and further comprising markings thereon relating to the diameter of a vessel upon which the band is placed, the markings being measured from the first end and whereby the measurement relating to the diameter is observed where the first end engages the tail portion.

\* \* \* \* \*